United States Patent
Bogema

(10) Patent No.: US 9,072,425 B1
(45) Date of Patent: Jul. 7, 2015

(54) METHOD OF PROVIDING A PROPER ON-SITE EVIDENCE CHAIN FOR A COMBINED DRUG TEST/DNA PRESERVATION PROTOCOL

(71) Applicant: Stuart Bogema, Collierville, TN (US)

(72) Inventor: Stuart Bogema, Collierville, TN (US)

(*) Notice: Subject to any disclaimer, the term of this patent is extended or adjusted under 35 U.S.C. 154(b) by 8 days.

(21) Appl. No.: 14/196,684

(22) Filed: Mar. 4, 2014

(51) Int. Cl.
*A61B 5/00* (2006.01)
*A61B 10/00* (2006.01)
*A61B 5/145* (2006.01)

(52) U.S. Cl.
CPC ........... *A61B 5/0022* (2013.01); *A61B 10/0051* (2013.01); *A61B 5/0077* (2013.01); *A61B 5/14507* (2013.01); *A61B 5/14546* (2013.01); *A61B 5/742* (2013.01)

(58) Field of Classification Search
CPC . A61B 5/0022; A61B 10/0051; A61B 5/0077
See application file for complete search history.

(56) References Cited

U.S. PATENT DOCUMENTS

| | | | |
|---|---|---|---|
| 6,248,598 B1* | 6/2001 | Bogema | 436/518 |
| 2004/0122353 A1* | 6/2004 | Shahmirian et al. | 604/65 |
| 2004/0138535 A1* | 7/2004 | Ogilvie | 600/300 |
| 2004/0184954 A1* | 9/2004 | Guo et al. | 422/56 |
| 2005/0143675 A1* | 6/2005 | Neel et al. | 600/583 |
| 2006/0154642 A1* | 7/2006 | Scannell, Jr. | 455/404.1 |
| 2007/0118399 A1* | 5/2007 | Avinash et al. | 705/2 |
| 2008/0292151 A1* | 11/2008 | Kurtz et al. | 382/128 |
| 2011/0264696 A1* | 10/2011 | Selaniko | 707/770 |
| 2012/0067144 A1* | 3/2012 | Slowey et al. | 73/864.73 |

* cited by examiner

*Primary Examiner* — Sam P Siefke
(74) *Attorney, Agent, or Firm* — Wyatt, Tarrant & Combs, LLP; William S. Parks

(57) ABSTRACT

A combination of an on-site drug testing protocol and effective secure evidentiary procedure to ensure veracity and chain of possession for prosecution purposes is provided. Additionally, the procedural method includes a combined secure adhesive attachment to a drug test that serves as both an information collector and preservation device. The overall method thus includes steps of having a test subject apply oral fluids to a test device, covering and sealing the device, and taking real-time information and photographs into a time-stamp system and supplying such information and photographs instantly to a secure database. The oral fluids are thus preserved by the information-providing seal under a proper cover component to ensure DNA material is permitted for authenticity purposes as well. The overall protocol thus accords an all-encompassing evidentiary chain model at a highly trustworthy level if needed in a courtroom setting.

3 Claims, 2 Drawing Sheets

METHOD OF PROVIDING A PROPER ON-SITE EVIDENCE CHAIN FOR A COMBINED DRUG TEST/DNA PRESERVATION PROTOCOL

FIELD OF THE INVENTION

The present invention relates to a combination of an on-site drug testing protocol and effective secure evidentiary procedure to ensure veracity and chain of possession for prosecution purposes. Additionally, the procedural method includes a combined secure adhesive attachment to a drug test that serves as both an information collector and preservation device. The overall method thus includes steps of having a test subject apply oral fluids to a test device, covering and sealing the device, and taking real-time information and photographs into a time-stamp system and supplying such information and photographs instantly to a secure database. The oral fluids are thus preserved by the information-providing seal under a proper cover component to ensure DNA material is permitted for authenticity purposes as well. The overall protocol thus accords an all-encompassing evidentiary chain model at a highly trustworthy level if needed in a courtroom setting.

BACKGROUND OF THE INVENTION

Narcotics, including such materials as marijuana, cocaine, and the like, continue to be a problem within society, particularly when used prior to a person driving a vehicle or present in public. Notably, although some items, such as marijuana, have become more acceptable in certain regions, there still exists a definitive effect associated with such a substance that impairs judgment and physical ability in certain circumstances. Certainly, such concerns are prevalent with other types of drugs (cocaine, heroin, methamphetamine, etc.) such that laws are in place almost uniformly around the country to prevent active usage of such potentially dangerous substances. Even with the burgeoning acceptance of *Cannabis* in certain locations, there still remains a legal basis thwart activities (such as driving, for instance) after exposure to such a legalized substance (much like there is prohibition for driving under the influence of alcohol). As such, there exists a need to provide not only an effective manner of testing individuals for the presence of such drugs within their system in general, but to do so in and under certain situations and circumstances that require immediate and careful analysis and recordation. Of particular importance is the ability to provide a suitable method of testing for such substances in a reliable manner, specifically as it pertains to actual usage by a person at the location of discovery. Such test protocols are typically requested and undertaken in response to the outward appearance and/or actions by an individual at a certain location, whether in a public place, behind the wheel of a car, or even within the confines of a dwelling or other like building. If there is probable cause to seek a test for such a purpose, the authorities may have the capability of testing as a result. Additionally, such situations also include employment requirements, corrections unit considerations, probation reviews, public school needs, and other locations that have drug-testing protocols for individuals.

One possible problem, however, that lurks behind the scenes of such a situation is the potential for an on-site test being challenged in a prosecution, arbitration, or administrative setting. In other words, even if an officer (or other like person or persons) properly requires, requests, and has performed an on-site controlled substance test of an individual (such as through the utilization of an oral fluid collection testing device), the lack of effective recordation and thorough control of such a test (and the result gleaned therefrom) has led to challenges to exclude such devices and results from evidence when, for example, such an individual is indicted and brought to trial for such an offense, fired or suspended from a job, or held liable for civil offenses, as merely examples. Generally, the utilization of on-site tests are limited in scope to the basic introduction of a test device within the mouth of the alleged drug user and then it is capped and placed into custody with minimal consideration for corroboration of person and test. The lack of effective guidance for an officer in such situations, as well, poses a distinct dilemma as there may be difficulties with the individual beyond a refusal to cooperate with the requested test, but also after such a test is undertaken. Although there is often utilized on-board video recording devices to aid in the presentation of a proper stop, inquiry, arrest, etc., by an officer or other authoritative person (particularly if the location of such a situation allows for such a camera to be aimed properly for such a purpose), the lack of exact views of the test device itself (such as serial number, recorded name of the officer and the tested individual, etc.) makes corroboration rather difficult even with such "eyewitness" accounts in place. Basically, even with a reliable test and ultimate positive result (for at least one controlled substance), an alleged criminal, in one example, may still have grounds to challenge the veracity of the overall protocol and measured drug levels in order to either bring into question the presentations made in court to that extent, or even to remove from evidence such devices due to a lack of definitive chain of evidence from officer to courtroom (e.g. the sample and/or records may be "tampered" with from the time of testing to the time such evidence is presented for courtroom review). Since the officer may simply record minimal information on/with the device subsequent to oral fluid introduction by an alleged drug user, and then such a device may be then merely deposited within a evidence collection device and/or area at the police station, without any further exact indications as to the identity of the subject perpetrator and the correlation between the test device and that person, specifically, the potential for attack by a defense attorney at any time (pre-trial, such as discovery and/or exclusionary evidence motions) remains relatively high. Furthermore, the potential that bad actors within the police department itself could possibly violate (or allow to be violated) a used test device by planting results thereon and/or therein while out of the testing officer's possession is at least an available inquiry by such a defense attorney if in a court setting, particularly without effective verification means in place to properly combat such an accusation. Many court cases, some famous, some certainly not as well known, have depended primarily upon circumstantial and, in some cases, direct evidence that has a questionable history due to interference with other individuals prior to discovery and/or actual trial. Thus, there exists a significant need to provide effective means to best ensure that chains of evidence or, at least, the test devices utilized in such situations are verifiable as relating not only to the specific person tested, but to a specific date and time at which the test was actually undertaken. As noted above, as well, such issues may and do arise in employment settings, jail situations, probationary situations, etc., such that the necessity for verified and reliable test results in this nature are universally needed and important for these similar reasons.

To date, there have been minimal activities in this area that have been developed to meet this issue. Breathalyzer tests have been utilized that allow for on-site testing for alcohol, certainly. Correlation, however, with the computerized system, and/or a video recording device permits greater flexibility with such devices to ensure that a specific person is actually tested on the date and time involved and the result is properly presented in an effective manner such that all such results are archived properly for courtroom needs. In those situations, the defense attorney may still attack the actual trustworthiness of the breathing test itself, rather than the chain of command over the evidence obtained from such a test method, since the computerized systems are given significant leeway in that manner. The problem lies with a base test protocol that is not directly tied to a computer device for "automatic" collection of information for criminal prosecution purposes. Time stamping with such a computerized system at least would allow for reliability as to the actual test sample coupled with a contemporaneous recordation by the same authority figure of the target person's identity; however, such requirements have not been provided beyond the breathalyzer result itself. As well, typical tests do not effectively permit collection and preservation of the test subject's DNA to permit verification of test subject to test result at a later date.

Beyond such a deficient test protocol, the prior art is limited to base test methods alone. Oral fluids have been collected and tested on the spot by authority figures with encapsulated test devices, certainly. However, as with breathalyzers, these past tests are limited to simple written recordations on the test device surface which may be altered or otherwise defaced during the time after testing to actual possible introduction within a trial in a courtroom setting. Again, although the test results are superlative, generally, with such oral fluid collection devices, the potential for attack by a defense attorney with regard to the reliability of chain of command of such a device within such a timeframe leaves a rather large opening in that regard. As such, it is important to ensure that the actual test results will be properly admissible in court and will also withstand a chain-of-command defensive strategy to destroy such evidence, or, at least, drastically reduce the usefulness thereof in court.

Thus, there remains a definite need to provide not only a reliable test device for certain narcotic substances present within the human body, but a simultaneous effective manner of guaranteeing, to a certain degree, at least, that such test results derived therefrom are reliably received, recorded, and eventually entered within a legal case as suitable evidence of the definitive presence of narcotic substances within a test subject's body at the specific time of testing. To date, again, such a desirous device and method have yet to be properly provided the pertinent industrial areas.

Advantages and Summary of the Invention

It is an advantage of the present invention to provide a reliable oral test protocol that allows for perpetrator cooperation and review during and after recordation to ensure test results and identifications are secured for future reference purposes. Another advantage of this inventive method is the ability to record such information within two separate devices for coordination and corroboration. It is an additional advantage that the inventive drug testing protocol provides tamper-proof measures in both a physical and electronic capacity to ensure identification of a perpetrator in relation to a specific drug test. Yet another advantage of this invention is the reliability of the system to apply time and date stamps to photographs and on-line documents, as well as the utilization of a seal that conforms to and confirms the specific test results and test subject identity.

Accordingly, the subject invention encompasses drug test/result recordation and test subject identification method, wherein said method includes, as components:

1) an oral collection immunoassay device including a collection end and a visual readout end, wherein said collection end includes a removable and re-attachable cover, wherein said device is utilized to collect saliva from a test subject's mouth in order to determine the presence and/or amount of analytes therein that indicate said test subject's use or nonuse of certain narcotics through inspection of said visual readout;

2) an optional specific seal implement including a unique and permanent identifier thereon in relation to the specific oral collection immunoassay device;

3) an on-line application that is instituted within a remote communication/photograph-taking device; and 4) a central record depository coordinated with said remote communication/photograph-taking device;

wherein said method involves the following steps:

a) subjecting a test subject to said oral collection immunoassay device in order to determine if narcotic use has been undertaken by said test subject, wherein said test subject applies a saliva sample from his or her mouth to an uncovered collection end and results are then provided within said visual readout end indicating use and/or amount of narcotics present within said test subject's saliva sample;

b) placing said cover over said uncovered collection end and, optionally, applying said optional seal implement over at least a portion of said covered collection end and a portion of said visual readout end simultaneously, wherein said seal implement does not impede viewing of said visual readout;

c) recording test subject information as well as said test results through accessing said on-line application within said to enter the test subject's identifying information, including written information and photographic information of the test subject, the test subject's identification, the entirety of said test subject's oral collection immunoassay device indicating the test results through said visual readout, and the optional applied seal implement, wherein all of said written and photographic information is recorded and date- and time-stamped within said remote communication/photograph-taking device; and d) transferring said written documentation and said photograph information from said remote communication/photograph-taking device to said central depository, wherein said information is date- and time-stamped at said central depository upon receipt thereby;

wherein said stored information is accessible for retrieval at a later date.

The method also includes a step wherein the seal implement is definitively utilized and placed over the collection end and recording the unique identification of said seal implement and providing written documentation of said test subject to said seal implement. Thus, when definitively utilized, such written documentation is properly recorded and transferred as in step "d", above, as well.

Such an overall test method allows for complete encapsulation of test subject test results and other information (both written and photographic) in such a manner that any tampering thereof will be noticeable from the time of test completion and entry within the central depository and retrieval thereof for evidentiary purposes. Because of the multi-layered approach for consistent proof of test veracity and test subject identity, even if one aspect appears to show evidence of questionable handling (or even tampering), the reliance on the remaining pieces of properly recorded and stored information would be sufficient to overcome such a potential issue. For instance, if the seal is utilized and is broken or removed from the test, the recorded photograph of the test would show the actual readout of narcotic levels within the test subject's system at the moment of testing. Coupled with the date- and time-stamped written documentation (such as name, address, age, seal number, etc.) and/or the photographic documentation (such as the test subject's picture, photograph of his or her identification, such as a driver's license, for example) would be sufficient to corroborate the actual undertaking of such a test for that specific person. If, however, the central depository files have been compromised in some manner (hacking, for instance), then the files date- and time-stamped on the remote communication/photograph-taking device (smartphone, tablet, etc., as examples) including the same types of information could be utilized for such corroboration purposes, if necessary. Additionally, the potential loss or apparent compromise of all such electronic files in either the central or remote devices could be remedied or supplemented by the proper preservation of the test subject's identifying DNA within the oral fluid collection device that has been covered and sealed to prevent tampering. In essence, the overall method allows for multiple levels of evidence preservation with a relatively straightforward and easy to implement overall protocol.

The particular oral collection immunoassay device is preferably one that permits such saliva collection, delivery, and analysis within a central transportable implement. In this manner, such a test allows for on-site (such as at a traffic stop, at a person's house, etc.) undertaking by an authorized officer that facilitates cooperation by a test subject and proper preservation thereafter. This type of implement thus must permit a test subject the ability to provide a saliva sample to a collection structure without the need for manipulation of the saliva or use of instrumentation outside of the implement. As well, as noted above, the implement must also provide for a visual readout of the results, i.e., the presence or absence of a particular analyte within the test subject's saliva. This aspect thus allows simple collection and analysis sequentially without further manipulation of the saliva sample or the device, as well as results indications at the location of testing within minutes.

Such a device also desirably provides for the collection of the saliva sample and the determination of analytes in a particular saliva sample outside of the typical laboratory setting by combining the two processes, collection and testing. Thus, the subject invention will allow for field tests by law enforcement for drugs of abuse and analysis of medicines and endogenous substances in saliva to be effected by non-laboratory personnel and for assays to be performed quickly and simply, i.e., without the need to involve a laboratory technician or setting. This should afford benefits both in terms of convenience and reduced costs.

Combining the collection of specimen and the analysis into a single device with no operations or reagents necessary will greatly simplify such testing and allow untrained users to perform such collection and analysis. With no manipulation of the device or addition of reagents, untrained users simply insert the collection end of the device into the mouth of the person from whom the saliva is collected. No further operations are required and the test results are read on the device by a visual readout, such as the presence or absence of a colored line in the test read area. Such simple testing of saliva thus permits testing outside of a laboratory setting and in a variety of locations, such as the roadside, police stations, prisons, factories, and other workplaces, the home, the hospital bedside, basically any desired (and presumably necessary location). Accordingly, such a testing device (implement) eliminates the need for costly laboratory testing procedures, which should result in considerable cost savings for the subject device, with highly reliable results.

The collection device thus provides a simple and direct means to collect saliva from a person's mouth into a drug assay component by means of one or more absorbent materials that extend out from one end of the device, which absorbent materials are placed in contact with saliva in the mouth. The saliva is collected because of the absorption and capillary flow of the saliva through the absorbent material into the device. Moreover, in the subject immunoassay device, such absorbent material or materials will preferably be directly attached to the solid support upon which the immunodetection reactivity for one or more analytes is effected. In this way, the simple collection of the saliva sample and initiation of the immunoassay for the analytes can be performed substantially contemporaneously, i.e., as soon as enough saliva has been absorbed to initiate contact with the solid support on which one or more immunoreactions is effected.

A cover, as noted above, typically a plastic cover, is part of the device, as well. The purpose of this cover is to protect the absorbent material that projects from one end of the device for the saliva collection. This plastic cover is removed prior to insertion of the absorbent material end of the device into the person's mouth. After saliva collection is complete, this plastic cover is replaced over the absorbent material end of the device to shield the absorbent material that contains saliva. Thus, this obviates the problem of potential contact by the testing person with the saliva in the absorbent material after the cover is placed on the device. This is significant, particularly in the context of detection of illegal drugs, when it is important that the results should be accurate and not subject to error because of potential contamination by an unskilled user, e.g., a law enforcement official. Additionally, such a cover should be placed on the absorbent end as soon thereafter the saliva sample is provided by the test subject without touching the absorbent portion to prevent any contamination thereof by any other person.

The oral collection test device provides a means to assay various analytes by the method of immunoassay on a solid support with visual readout for saliva specimens. The subject invention allows for the detection of analytes even in low concentrations, e.g., as low as about 1 ng/ml to 500 ng/ml, in saliva by a simple visual read of the result area(s) on the solid support. Visual readout is obtained by use of tracers that contain a colored label such as colored latex particles, colloidal metals or liposomes containing a dye. This invention allows simple collection and testing of saliva for specific analytes in a single device. As noted previously, the present invention provides an immunoassay device that provides for both saliva collection and analysis which requires no operation or reagent additions other than the simple collection of saliva via absorption by the device from the mouth. Thus, the device allows collection and testing of saliva for various analytes by unskilled users in remote locations.

The main problem facing utilization of such an oral collection immunoassay device is the potential for corruption of the results after testing, particularly if such a test is undertaken in relation to an on-site driving or other like incident. The overall method described above thus retains the capabilities of such a desirable test implement while best ensuring such test results will be presentable as proper evidence in a courtroom setting should such a need arise. The combined test results with proper recorded written and photographic evidence, as well as the preservation of any DNA from the test subject's saliva sample provides, as noted above, this multi-level protective approach for evidence trustworthiness. Even if one component (or even two components) of these multiple protective measures become compromised in some manner, the retention of at least one measure would provide suitable evidentiary veracity.

The seal implement may thus be of great importance to not only provide another manner of identifying the actual test result and link the same to a specific test subject through a unique seal implement identifier, but the placement of such a seal implement over at least a portion of the oral collection immunoassay device's collection end with simultaneously application to a portion of the visual readout end would provide tampering evidence if such is removed or otherwise distorted. The saliva sample from the test subject can thus be utilized not only for the detection of analytes in relation to certain narcotics, but also to retain DNA of the same person. Certainly, such an identifier itself is considered one of, if not the, most reliable means to distinguish one person from another. If such is properly preserved in this manner, then such a result may provide highly effective corroboration of the test subject's identity, at least, in relation to the test results. The seal implement itself may be provided in relation to each oral collection immunoassay test device supplied an officer (or other like-situated authorized person) with specific identifying marks (such as permanent printed sequential numbers, printed unique alphanumeric character sequences, and the like) that can be properly recorded with the test subject's information (name, address, age, etc.). Additionally, such a seal implement may include an extra amount of space for the officer (or other like-situated authorized person) to place other identifying marks (test subject name, address, etc.), if desired for another level of insurance of such an issue. The seal implement should also include an adhesive component that allows for removal from a supply source (such as a roll or sheet of seals in label form) but that, when applied to the materials of the oral collection immunoassay test device and the cover for the collection end, any removal or other type of like activity (such as scraping, scratching, cutting, etc.) will be clearly evident. In this manner, then, such a seal implement component within the overall method allows for protection to both the test subject and the authorized officer (or other person). The test subject is thus provided a means to show that tampering with the seal would bring into question the trustworthiness of the overall sample. The officer is provided a means to corroborate truthfulness of the test results for the specific test subject if the untampered seal shows underneath a specific DNA determination aligned with such an alleged perpetrator. Furthermore, the recordation of the seal identifier within the remote communication/photograph-taking device and thus the central depository, if needed, would further prove the trustworthiness of the sample since any change in the seal identifier (for instance, if it is fully removed and another seal is then placed where the first one was over the two ends of the test device), would show the seal was tampered with. As well, if the photograph of the seal implement in place on the test device is taken and properly date- and time-stamped within both remote and central systems, then any different appearance (placement, angles, etc.) in comparison with the original photograph thereof could be evidence of tampering, at least potentially. In other words, such a seal implement provides overall protections on both sides.

The remote communication/photograph-taking device is important within the present invention specifically because of the capability to record distinguishing features/informational aspects of the test subject directly at the test location. Such a device may be a cell phone (such as a smartphone, Android, etc.) that allows for not only the ability to properly and clearly photograph a person's face, a person's identification card (such as, without limitation, a driver's license), and the test device, itself, both in its entirety to show the readout results, and also to show the seal implement in place for number identification. A tablet-type device may also be utilized for this purpose, although for ease in handling, activating, and movement during a traffic stop or other type of roadside or other potentially awkward location (at least for such an offsite test and/or interrogation situation). Such a device thus needs a direct link to a central depository for recordation purposes, as well as a means to properly date- and time-stamp all entered information/photographs onto the device for storage and/or transfer purposes. Although such a device may already include such date- and time-stamp capabilities on its own, and thus that may add another layer of protective evidentiary measures in this situation, preferably the device has been outfitted with a suitable protective application that not only achieves such a result internally, but also allows for secure transfer of all recorded information (written and/or photographic) to a central depository. Such an application is thus provided in secure fashion and may be either supplied within an already-outfitted communication device to the authorized officer (or other like person) or downloadable in a secure format by the same person. Access from the communication device is thus permitted through proper clicking (or otherwise entering a command) on the device (either, for instance, and app icon or a bookmark, depending on the type of device in use) and providing a username and password (or other similar type of access protocol). The system may be set up to permit access by the officer (or other like person) automatically after a single entry every number of days (basically to permit direct link to the system without the need for potentially cumbersome password, etc., entries while in the midst of subduing an alleged perpetrator), such as every 30 days, as one example. In any event, the application would then lead to a series of screens requiring quick response before moving to the next screen. Initially, then, the application would inquire as to the status of the oral collection immunoassay test device and its administration. If yes, then the system leads to a screen requesting labeling of the test device with the current date and the identification number (DL, for instance) and then a photograph of the test results on the device. The photograph could thus be taken and then the communication device may be "browsed" to locate that specific photo file for transfer or copy to the application. Otherwise, the application may simply allow for a photograph to then be taken and directly transferred and/or copied in the same manner. Thus, an entire photograph of the test may be taken and supplied in this manner. The same could then be undertaken for the area including the seal implement in place thereon. With either photograph, if such is out of focus and insufficient for whatever purpose, the user may take another series as needed. Since the application and the device itself would provide date- and time-stamps thereof such information, the photographs, whether first or second or later, of the same subject matter would be properly recorded for evidentiary purposes. Certainly, if the user decides to photograph one or the other first, or even subsequent to any other photographs and/or other written documentation, there would be definitive issues hampering such a situation. In other words, the application may be configured to request any subject photographs at any time during the overall activity; in this potentially preferred instance, the test device has been noted as being photographed/recorded first.

Otherwise, and preferably subsequently, then, the officer or other user (such as a corrections officer, employer testing individual, etc.) is then directed to photograph the test subject's driver's license (or other identification documentation showing his or her identity). The same capability of photographing as many times as necessary for a suitable result, as above, may be undertaken. If the test subject does not have a driver's license, or any other type of identification, then, as alluded to above, the DNA result from the saliva sample may be used for identity corroboration, if necessary. The application then requests a photograph of the actual test subject, to be handled in the same manner as above, as well. The photographs are then either sent to the central depository at this time or retained until a further documentation step is completed.

The application then may request specific information about the test subject to be typed (defined herein as "written documentation") on the communication device screen for capture, storage, and, ultimately, transfer to the central depository. Thus, at least in terms of the information supplied by either the test subject directly or through his or her identification documentation, the subject's first name, last name, license number, and test results indications (to corroborate the visual readout results). Additionally, the specific date and time noted on the communication device may then be transferred, either directly by the application or through entry manually (e.g., typed) by the officer (or other user) to be used as a corroborative notification with the date- and time-stamps of the other recorded information within the communication device and/or into the central depository.

Thus, when completely entered, the application requests submission through a click or other means that effectuates transfer of all such entered information (written and/or photographic) from the communication device to the central depository. Such a depository may be situated in any manner that is securely protected and that allows for such individual transferred information to be sequestered into individualized files that are date- and time-stamped to indicate receipt and collection of all such information within a single compilation. Additionally, the depository allows for retrieval of all such filed information through a proper retrieval program to those ends. Once the depository receives all such information, a response is generated and sent back to the communication device indicating such a submission has been properly received, recorded, filed, and saved, in any manner (such as a simple "Results have been saved" notification, for instance).

The depository may be housed within a server and/or database located, again, at any desired secure location. Such may be in association with a specific law enforcement agency or otherwise through a contracted entity to such an end. The ability to send such information digitally and wirelessly is certainly needed to that extent, as well. Thus, the depository is typically to be run through the utilization of at least computer program to effectuate these necessary actions. In this situation, then, the term "computer program" or other like description is intended to denote that the overall method is controlled by software code and through the utilization of a computer machine (or the like) for implementation and utilization. The present invention may be implemented on a program or code that can be stored in a computer-readable (or electronically-readable) medium and that can be provided in a WAN environment. The overall system may be implemented onto a server using, as non-limiting examples, Apache web server, MySql on Linux, Oracle on Linux, Java servlets, Applets, HTML, JavaScript, Java, C#, and Microsoft's .NET, in such a manner as a user would have access to the depository (e.g, server, for instance) on demand through a secure connection (for submission and/or retrieval thereto and/or therefrom). Such a server may reflect implementation on the Internet, an intranet, or an extranet, and, again, could be accessed through wireless technology, preferably, or even through a dedicated server system that receives such information through signals transferred from a separate middle server. Thus, the middle server may receive the wireless signals from the communication device and then relay such signals to the connected server and/or data-base (depository). Any software platform may thus be employed to implement the underlying algorithm system, such as JAVA, Linux, and the like, and the code itself may be written in any language, including, BASIC, COBOL, C+, C++, and the like. As well, the term "central depository" is understood to encompass any configuration in which the final storage server is in place for such a purpose and any middle relay sources may be provided to ultimately reach such a destination from the remote communication device of the user (officer).

DETAILED DESCRIPTION OF THE DRAWINGS AND PREFERRED EMBODIMENTS

Without any intention of limiting the breadth and scope of the overall inventive method, the following descriptions of the accompanying drawings provide one potentially preferred embodiment of the utilization of the aforementioned inventive method.

Figure 1:
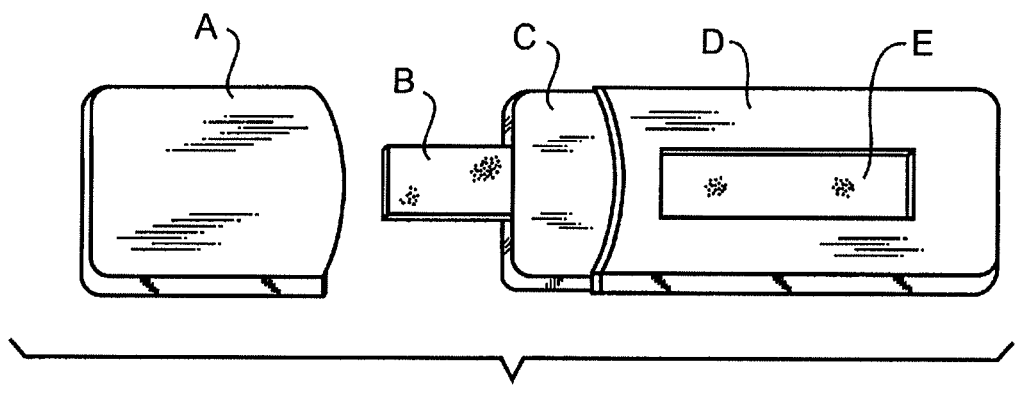
FIG. 1 provides a top view of a potentially preferred oral collection immunoassay test device for utilization within the inventive method.
Figure 2:
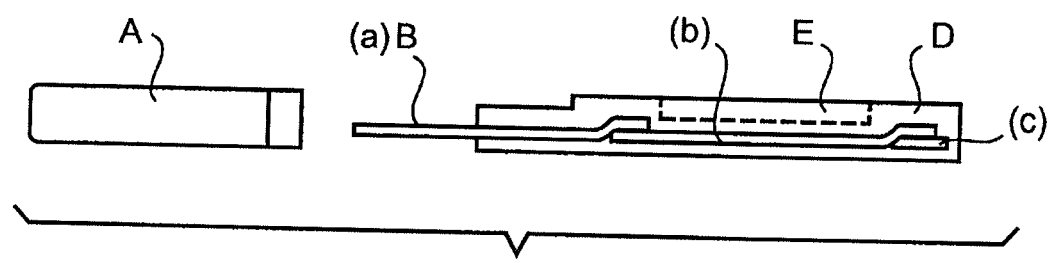
FIG. 2 shows a side view of an assay device according to the invention which comprises a single saliva collection and assay component "B".

FIGS. 1 and 2 show one embodiment of a potentially preferred embodiment of the test device for utilization within the inventive method, as seen in top view, wherein the subject saliva device comprises a single saliva collection and assay component area "B". In the Figure, "A" depicts an optionally removable cover, typically made out of a plastic material, that optionally covers the saliva collection end and assay component portion of the device B. In the Figure, "C" refers to the end of a holder "D", typically comprised of a plastic material, which holder keeps the saliva collection and assay component(s) B, in place and provides a means to hold the device while inserting into the mouth for saliva collection. The plastic cover D has a cutout portion "E" that allows viewing of the portion of the saliva collection and assay component(s) B, on which the immunochromatographic assay(s) take place and the visual readout is accomplished.

Such a device may be configured to include two saliva collection and assay component areas, ("B"), and two cutout areas ("E"), in the holder D, in which visual detection results can be seen after an assay has been completed, as well, if desired (and thus within another potentially preferred test device for the inventive method).

Thus, in FIG. 1, the reference letter "A" shows the cover for the device, the reference letter "B" shows the saliva collection and assay component(s), the reference letter "C" shows the end of the plastic holder over which the plastic cover "A" fits snugly, the reference letter "D" shows the holder for the device, and the reference letter "E" shows the cutout(s) in the holder "D" through which the test read area of "B" can be seen. The assay component contains the reagents (binders, tracers and any others) for the immunochromatographic assay(s) and the test read areas. As well, the area between the collection portion and the assay component includes sufficient contacts and materials able to assure the complete capillary flow of a portion, at least, of a saliva sample there through.

More specifically, the "(a)" portion will preferably be comprised of any absorbent material that is able to be safely placed within a subject's mouth, that provides for sufficient absorption of saliva for the saliva to flow onto the "(b)" portion, the solid support on which the immunochromatographic assay is conducted. By sufficient is meant that saliva will be sufficiently absorbed after being placed for a sufficient time in a user's mouth, e.g., about 10 to 120 seconds, with sufficient saliva typically being at least about 0.2 to 4 ml.

Suitable absorbent materials include by way of example nitrocellulose, cellulose acetate, polyethersulfur fabric, paper, fiberglass, polycarbonate, polypropylene, acetate, chemically modified paper, and combinations thereof, e.g., glass fiber containing cellulose material, or other materials providing good lateral flow rates of saliva. The absorbent materials allow lateral flow of potential analytes contained in the saliva.

Typically, the "a" portion that is placed inside the subject's mouth and which provides for saliva collection will range in length from about 0.5 to 4 cm, have a width of about 0.8 cm to 4 cm, and a thickness ranging from about 0.1 to 0.4 cm. However, these dimensions may vary widely largely dependent upon the particular user's mouth and specifically the varying mouth size of different users, e.g., children versus adults. The material of "a" may further comprise a support material such as Mylar attached to improve strength.

As noted above, the "(a)" portion of "B" will optionally be covered by a detachable cover, typically comprised of a plastic material, that preferably will fit snugly over the device, and will prevent "(b)" from being contaminated after saliva collection has been effected. This cover is not mandatory as other precautions can be taken to prevent contamination of saliva and the saliva collection portion of the device after use. This cover "A", if present, will typically range in length from about 1 to 7 cm, width of 1.5 to 9 cm, and thickness of about 0.2 to 2 cm, and will be designed such that it fits snugly over the device, specifically covering up to the "C" portion of the device. The "A" cover can alternatively be comprised of other materials such as cardboard, or metals such as aluminum.

The "(b)" portion of the device is where the immunochromatographic reaction takes place that provides for detection of one or more analytes, and on which visual readout is accomplished. This area will comprise a solid support, comprised of an absorbent material that allows for immunochromatographic assay of saliva by capillary flow that includes a visual reading area on which is directly or indirectly bound one or more of the following; 1) a binding partner, typically a protein such as an antibody that specifically binds an analyte; 2) a "tracer" that is comprised of a ligand (the analyte) labeled with a colored particulate label; and 3) a "visual read area" or "test read area" that comprises at least a first area on the solid support portion "(b)" that provides a visually detectable line or other visible area, e.g., circle, triangle, square, etc., when the assay is complete that provides an indication of the presence or absence of analyte; and optionally a second area, also on the solid support within the visual read area that results in a visually detectable control line or other detectable portion when the assay is completed for the respective analyte.

As can be seen within FIG. 1, the "(b)" area is held inside the holder "D". The "(b)" area will preferably comprise a solid support strip, comprised of an absorbent material, e.g., selected from the above-identified materials, contained within a casing "D" that typically ranges in length from about 2 to 25 cm, width of about 1.5 to 8 cm, and a thickness of about 0.2 to 1.5 cm.

These materials include, in particular, nitrocellulose, fabric, nylon, cellulose acetate, or any other material on which the desired immunochromatographic assay can be effected. This requires that the material allow saliva and analyte in the saliva to flow through it and also support the requisite reagents, binders, tracers, and any other materials necessary for immunoassay.

More specifically, the solid material that comprises "(b)" will be a material that has a surface area (area/weight of material) that allows for the binder to be supported in a concentration (weight/unit area) such that the tracer is visible under assay conditions. The term "visible" means that the label on the tracer can be seen without the need for extraneous instruments, i.e., by use of the naked eye. The visibility of the tracer in visual read area of "(b)" allows for the determination of the presence or absence of the tracer, and/or the intensity of the visible tracer. This, in turn, allows for the determination of the presence or absence of analyte, based on the presence or absence of such visually detectable signal, e.g., colored line. Also, the intensity of the visually detectable signal provides a semi-quantitative means of determining the relative amount of the analyte being detected in the saliva sample, e.g., an illegal drug, therapeutic drug, endogenous biomolecule, alcohol, biometabolite, etc.

As noted previously, at least one portion of the strip "(b)" will be exposed by a cutout "E", in the plastic holder "D", which includes the read area of "(b)". The material of "(b)" can be nitrocellulose, fabric, nylon, cellulose acetate or any other material on which the assay can be effected. Moreover, the material will also allow the saliva and analytes in the saliva, to flow through it while supporting the reagents, binders, tracers and any others, for the immunoassay for the analyte(s).

The binder(s) which is supported on the solid support strip "(b)" is either a binder for both the analyte(s) and tracer(s), or a binder(s) for only one of the analyte and tracer, with the type of binder(s) which is used being dependent upon the type of assay which is being utilized for determining the analyte(s). For example, if the assay(s) is a competition type of assay, then the binder(s) supported on "(b)" would be a binder(s) for both the tracer(s) and analyte(s), whereby both tracer and analyte would compete for a limited number of binding sites on the binder.

If the assay is a so-called "sandwich" type of assay, then the binder(s) which is supported on the solid support "(b)" is a binder(s) for only the analyte(s). In such an assay, the tracer(s) is a tracer which is specific for the analyte, whereby tracer is bound to the analyte which is bound to the supported binder.

If the assay is an inhibition type assay, then the supported binder(s) is specific for only the tracer(s), and the tracer is also specific for the analyte. In such an assay, the presence of analyte inhibits binding of tracer to the supported binder. Thus, the tracer when bound to the solid support "(b)" is either directly bound to the binder on the support or is bound to analyte which is bound to binder on the solid support "(b)".

The type of binder(s), which is(are) used in the subject assay, is(are) dependent upon the analyte(s) to be assayed, as well as the specific assay procedure. As known in the art, the binder(s) which is(are) supported may be an antibody including monoclonal antibodies, a binding fragment thereof, an antigen, a protein specific for the material to be bound or a naturally occurring binder.

The binder(s) is supported on the solid support "(b)" in the test read area by applying a solution of the binder(s) to a defined area of the solid support, such as, for example in the form of a line, circle or other area. The concentration of the binder(s) placed in the defined area of the solid support "(b)" will vary depending upon the assay(s) to be performed; however, the binder(s) is(are) generally present in a concentration of at least 1 microgram/square centimeter and, preferably at least 40 microgram/square centimeter. The test read area may contain more than one test area, either with the same binder being applied to each test read area, optionally with different affinities and/or in different concentrations, or the various test areas may include different binders, in which case, the device may be used for determining more than one analyte on a solid support strip "(b)". The device may contain more than one solid support strips "(b)" for additional analytes or determining one analyte in various concentrations. Although the binder(s) may be appropriately applied to the test area(s) of the solid support strips "(b)" for support thereon by adsorption, it is also to be understood that in some cases it may be necessary or desirable to provide for covalent coupling of the binder to the solid support "(b)".

The ligand(s) which is labeled for use as the tracer(s) in the assay(s) of the present invention is also dependent upon the analyte(s) to be assayed, as well as the assay procedure. For example, if a competitive assay is being used for determining antigen or hapten, the ligand used in producing the tracer(s) would be either the analyte(s) or an appropriate analog thereof. If the assay is a "sandwich" type of assay for an antibody, then the ligand(s) used in producing the tracer(s) would be a ligand which is specific for the analyte to be assayed.

In producing the tracer(s) the ligand(s) is labeled with a particulate label, which is visible, whereby the tracer(s), when used in the assay, is visible. This type of label may include stained bacteria, colored latex particles, hydrophobic dyes, colloidal metals able to bind proteins when adjusted to the optimal pH and concentration (gold, silver, platinum, copper, and the metal compounds sodium hydroxide, silver iodide, silver bromide, copper hydroxide, aluminum hydroxide, chromium hydroxide, vanadium oxide, arsenic iodide, manganese hydroxide and the like). Methods for coupling colored particles to proteins are well known to those skilled in the art and are described in the afore-cited references.

As explained previously, the material of "(b)" allows the saliva to flow through it while supporting the reagents (binders, tracers and any others) for the immunoassay for the analyte(s). Thus, the solid support "(b)" for the reagents has capillary properties and is able to assure the elution of the colored bioselective reagents thanks to the action of the capillary forces at the saliva passage. The test read area of "(b)" optionally includes a test area that will visually indicate when the test has finished. Such an area is called a "Test Valid" area and includes an area on the solid support "(b)" where a binder is supported that will bind tracer to the extent that a visual area, such as a line or circle, will be produced when the device has completed the analysis for analytes. Therefore, there will be within the test read area of the solid support strip "(b)" (preferably) one or more areas that will show visual read areas for the analyte(s) and optionally one or more for the Test Valid visual read.

As also noted previously, the "(b)" area will be in contact with a "(c)" area, at least at one end. This "(c)" portion is comprised of material that allows for substantially all of the collected saliva to flow towards the end of the device opposite the end that saliva is collected. Therefore, the material that comprises "(c)" will desirably be one that allows the capillary flow of saliva towards the end of the device opposite from the collection end. Typically, such materials will be highly absorbent, with examples thereof including fabric, paper, cellulose, and other absorbent materials previously identified that will absorb the saliva as it flows through "(b)" by capillary action into the attached "(c)" material. The material of "(c)" should desirably absorb a relatively large amount of liquid relative to its weight.

Therefore, based on the design of the subject device, the only required operating steps for using such device to effect an assay is removal of the cover "A" (if present), insertion of the collection end of the device into the mouth, removal of the device from the mouth, replacement of the cover "A" (if present), and visual readout of the results of the device, preferably after the Test Valid areas show that the assay(s) is complete. In general, the assay will be complete anywhere from about 1 minute to 60 minutes after saliva collection. With certain narcotics, and particularly in relation to roadside and like testing (such as for perpetrators thought to be driving while impaired and under the influence of illegal substances of these types), such a time frame is preferably from 1 to 5 minutes, for evident reasons.

Accordingly, the subject device provides for the collection and assay of saliva specimens in a single step with no manipulation of the specimen nor instrumentation for reading of the assay results. Moreover, the device preferably will have a cover that functions to shield the saliva collection portion of the device both before and after saliva collection.

Compounds which can be analyzed according to the subject invention include, by way of example, drugs of abuse such as heroin, cocaine, marijuana, etc., nicotine and metabolites, human endogenous substances such as hormones, and therapeutic drugs. Other specific examples include, by way of example, tetrahydrocannabinol, cocaine, morphine, benzoylecgonine, heroin, acetylmorphine, amphetamine, methamphetamine, phencyclidine, diazepam, alprazolam, triazolam, 11-nor-delta-9tetrahydrocannabinol-carboxylic acid, LDS, oxazepam, other benzodiazepines, butalbital, pentobarbital, secobarbital, amobarbital, butabarbital, phenobarbital, methadone, propoxyphene, methadone metabolite, nicotine, cotinine, phenytoin, theophylline, antidepressants, digoxin, antipsychotics, antibiotics, tumor markers, steroids, ethanol, methanol, anabolic steroids, anti-tumor chemotherapeutics, anti-epileptics, environmental toxins, industrial pollutants, industrial chemicals, anti-arrhythmic medications, anti-hypertensive medications, metals, methylenedioxyamphetamine, methylenedioxymethamphetamine, sedatives, tranquilizers, central nervous system depressants, and narcotics.

The invention also refers to a method for the simultaneous collection and assay of saliva for the determination of one or more analytes in the saliva. The method and the device of the invention allow the collection and analysis for analytes with one direct collection of saliva from the mouth and subsequent direct and clear reading of the results visually. The method and the device preferably allow collection and determination of analytes in saliva in ten minutes or less and with high sensitivity. The device can be part of a kit that includes instructions for the use of the device and method. The following Example illustrates the present invention in a non-limitative way.

Test Device Example

A piece with dimensions of one centimeter by four centimeters was cut out of a ONitroPB nitrocellulose membrane with 8.0 micron pore size (Micron Separations Inc.). A piece with dimensions of one centimeter by 4.5 centimeters was also cut out of a MagnaGraph Nylon membrane with 5.0 micron pore size (Micron Separations Inc.). This membrane has added to it specific binders for analyte(s) of interest, in particular cocaine and tetrahydrocannabinol, in separate lines that will be in a Test Read area and a binder to trap excess antigen in a line in the Test Valid area. Tracers of colloidal gold conjugates of cocaine and tetrahydrocannabinol were added at the end of the membrane that will contact the NitroPB wick at the collection end of the plastic holder. A piece of highly absorbent paper measuring one centimeter by one centimeter was cut. The plastic holder and plastic cover are manufactured by means of injection molding from polystyrene which contains recesses for the contour of the NitroPB, the MagnaGraph Nylon and the absorbent paper. The plastic holder consists of two pieces, a bottom piece and a top piece. The NitroPB membrane, the MagnaGraph Nylon membrane and the absorbent paper are aligned in the bottom of the plastic holder in the recess contour. The NitroPB membrane extends 1.6 centimeters outside of the collection end of the plastic holder, the MagnaGraph Nylon was placed 0.5 centimeters under the other end of the NitroPB membrane inside the plastic holder bottom. The end of the MagnaGraph Nylon membrane placed under the NitroPB membrane contains the colloidal gold tracers for cocaine and tetrahydrocannabinol. Buffers and other reagents for stability were placed on the MagnaGraph Nylon membrane with the tracers. The absorbent paper was placed under the opposite end of the MagnaGraph Nylon membrane at the end of the bottom part of the plastic holder opposite of the collection end. The top of the plastic holder was placed on the bottom and snapped into place to firmly hold the membranes and paper in the proper place. The plastic cover is placed over the collection end of the assembled plastic holder. The dimensions of the entire device are 9.5 centimeters long, 2.5 centimeters wide and 0.8 centimeters thick. The entire device is sealed in an airtight foil pouch that contains a desiccant. The foil packaged device and instructions are packaged in a box.

In order to carry out a test for cocaine and tetrahydrocannabinol in a saliva specimen, the device was removed from its foil pouch and the plastic cover removed. The collection end of the device with the NitroPB membrane extending out was placed into an individual's mouth for sixty seconds. The device was removed from the mouth and the plastic cover replaced on the collection end of the plastic holder. The device was allowed to complete the assay for approximately three to eight minutes, when the Test Valid area of the Test Read window showed a visible red line. Adjacent to the Test Read area of the MagnaGraph Nylon membrane on the plastic holder was marked THC and COC. The presence of a red line next to the THC marking indicates the saliva does not contain a detectable concentration of tetrahydrocannabinol. By contrast, the absence of this red line indicated that the saliva specimen did contain a detectable concentration of tetrahydrocannabinol. The presence of a red line next to the COC marking indicates the saliva does not contain a detectable concentration of cocaine. By contrast, the absence of this red line indicates that the saliva specimen does contain a detectable concentration of cocaine.

Thus, such an Example allows for implementation within an official test protocol for an arrested perpetrator (for example) or any other person for which such a test for illegal drug use or unlawful levels of narcotics, etc., in the bloodstream during an activity (such as, for example, driving a vehicle with a certain amount of narcotics within his or her system). As alluded to above, in such circumstances there resides need to ensure such results are properly handled and transferred for reliable storage prior to a courtroom (or like evidentiary tribunal) so as to guarantee such results will be sufficient and accepted for evidentiary purposes. The inventive method thus includes the utilization of the above-mentioned test device as the base test with the remaining steps described further below.

Figure 3:
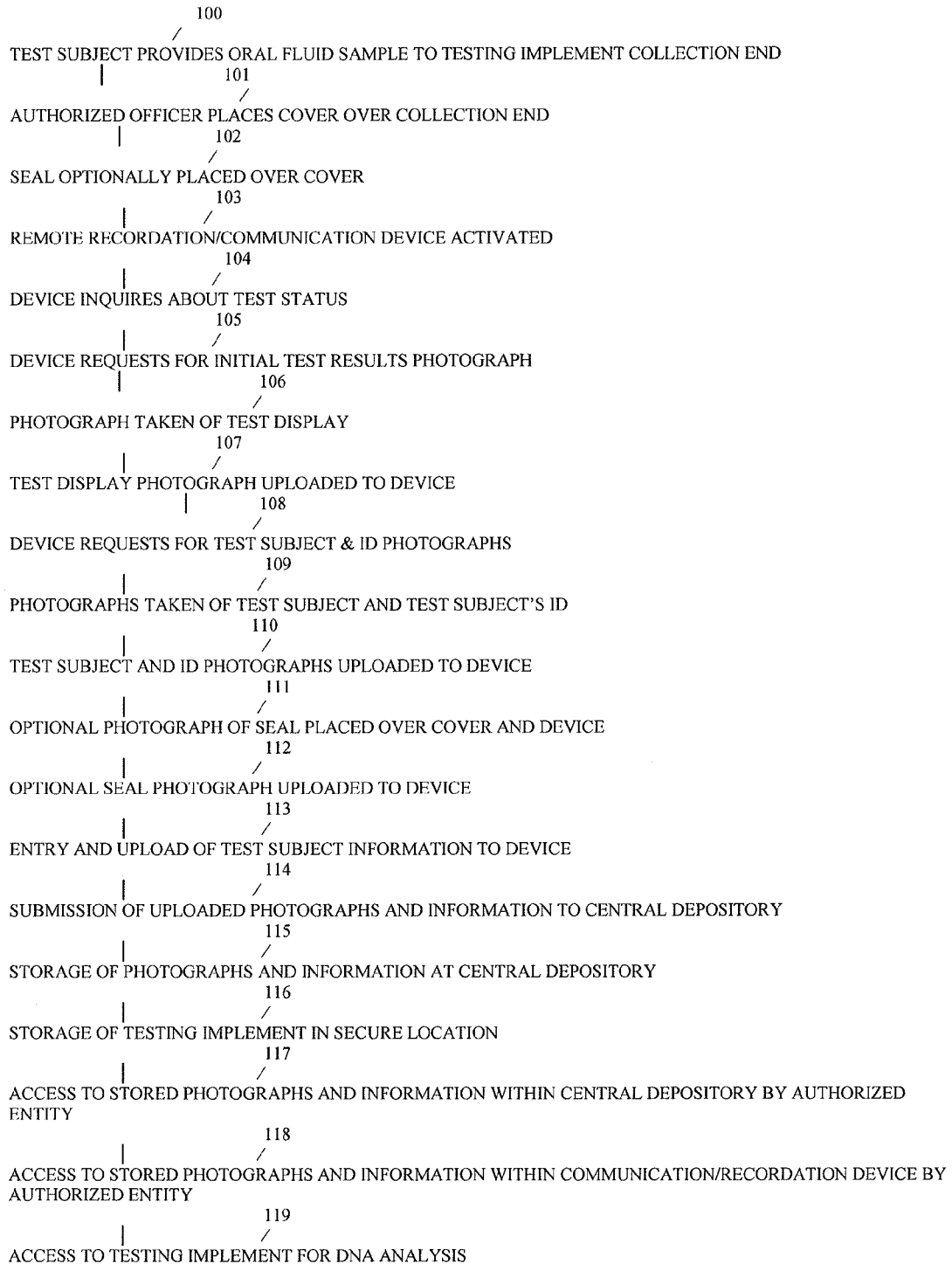
FIG. 3 depicts a flow chart of the steps of the overall inventive test result generation/evidence preservation method.

FIG. 3 thus shows a flow chart setting forth the complete test steps for this test/evidence preservation protocol. Step 100 is the utilization of the test implement (device) described in FIGS. 1 and 2, above. Step 101 indicates the placement of the cover over the oral collection end after a sample is taken, preferably by an authorized officer (whether a police officer, corrections officer, physician, nurse, employment drug testing individual, and the like) in order to preserve the collection portion. The next step, 102, then includes the optional, though, in some embodiments, present and actually preferred, placement of a seal implement to the over the replaced cover as well as at least a portion of the remaining test device (but not to impeded review of the display); further optional is thus the placement of a written identifier (or identifiers) to the seal surface itself, with such a written identifier(s) to correlate to the test subject. Step 103 depicts the subsequent activation of the remote communication device and the evidence recordation (preservation) application included therein. After activation, Step 104 shows the initial inquiry provided by the communication/recordation device regarding the status of the oral drug test. Upon proper affirmative reply, 105 shows the request from the device for photographic evidence of the test results; 106 includes the taking of the photograph with step 107 then showing the subsequent uploading thereof such a photograph (or photographs, as necessary) to the communication device application (with a date- and time-stamp included therein with such a step for recordation within the communication device itself). Step 108 then shows the request for a photograph of the actual test subject (whether an alleged perpetrator, inmate, medical patient, employee, etc.) as well as, whether within the same basic step or a sequential step, as the case may be, with no particular order necessary for proper functioning herein, a photograph of the test subject's identification documentation (such as a driver's license, social security card, and the like). 109 thus indicates the actual photographs being taken and 110 the uploading (with date- and time-stamp, again) of such photographs onto the communication/recordation device. Step 111 thus provides for the optional photograph of the seal implement in place on the test device, applied simultaneously to both a portion of the cover and a portion of the visual readout portion, but not to the extent that the seal covers or otherwise impedes viewing of the readout display. Step 112 indicates the uploading, again, optionally, although in some embodiments preferred, of the photograph of the seal implement with identifications thereon to the communication/recordation device (with time- and date-stamping, as above). Step 113 then allows for the user to then enter the information of the test subject, same as full name, address, age, and test results, as well as the time and date such information is entered, into the application on the communication device. Subsequently, after the information is entered as completely as possible, the user can then submit all such uploaded photographs (107, 110, 112) and information (113) to a central (computerized) depository 114 through wireless protocol, wherein the depository program generates and sends receipt of such information in a single file format (or, if desired in a split file format, as long as retrieval of such submitted is permitted in complete manner from either single or split files) with its own date- and time-stamp upon such receipt. Thereafter, in Step 115 the information is thus stored within the depository in such single or multi-file format, as desired, within a suitable secure server. In Step 116 the test device itself is also stored within a secure vault (or like article) for further use as evidence against the test subject, if needed.

Step 117 thus allows for access to the stored information from the central depository pertaining to the specific file (or files) including such information of the test results and identification of the pertinent test subject in relation to such test results. Step 118 thus indicates accessing of the correlated information from within the user's remote communication device, if necessary, for such a purpose, as well. Lastly, Step 119 pertains to the access to the test device in order to test the preserved DNA sample from the test subject's saliva sample that has been properly stored and preserved under the cover and the seal implement.

In this manner, the entire evidence preservation protocol permits suitable recordation of identity and test results for narcotics at the test site with proper deposit of such information within a central, secure, computer program evidence depository. With dual time- and date-stamping at the remote communication/photograph-taking device and the central depository, proper protections of such information at the exact time and date undertaken is recorded and preserved as well. With the seal implement in place to further assure of the date and time of such a test, and evidence of tampering of the test results thereafter, an overarching evidence preservation protocol is provided. However, in case any of these protective measures is compromised in any way, the resiliency of any of these measures may be sufficient to still provide the necessary evidence of test results for that specific test subject at a specific time and date. As such, with a suitable on-site oral collection immunoassay test device in operation, the results obtained therefrom will be sufficiently protected for evidentiary preservation purposes through the utilization of this effective method.

Such a system may thus be utilized within any situation in which drug testing is needed, whether, again, in terms of law enforcement, corrections, employment, medical treatments, and the like, with such tests administered and recorded by police officers, corrections officers, employment officers, physicians, nurses, basically any person for which such activities are deemed necessary for test subjects.

The preceding examples and descriptions are set forth to illustrate the principles of the invention, and specific embodiments of operation of the invention. The examples and descriptions herein are not intended to limit the scope of the inventive method. Additional embodiments and advantages within the scope of the claimed invention will be apparent to one of ordinary skill in the art.

What is claimed is:

1. A drug test/result recordation and test subject identification method,
   wherein said method includes, as components:
   1) an oral collection immunoassay device including a collection end and a visual readout end, wherein said collection end includes a removable and re-attachable cover, wherein said device is utilized to collect saliva from a test subject's mouth in order to determine the presence and/or amount of analytes therein that indicate said test subject's use or nonuse of certain narcotics through inspection of said visual readout;
   2) an optional specific seal implement including a unique and permanent identifier thereon in relation to the specific oral collection immunoassay device;
   3) an on-line application that is instituted within a remote communication/photograph-taking device; and
   4) a central record depository coordinated with said remote communication/photograph-taking device;
   wherein said method involves the following steps:
   a) subjecting a test subject to said oral collection immunoassay device in order to determine if narcotic use has been undertaken by said test subject, wherein said test subject applies a saliva sample from his or her mouth to an uncovered collection end and results are then provided within said visual readout end indicating use and/or amount of narcotics present within said test subject's saliva sample;
   b) placing said cover over said uncovered collection end and applying said seal implement over at least a portion of said covered collection end and a portion of said visual readout end simultaneously, wherein said seal implement does not impede viewing of said visual readout;
   c) recording test subject information as well as said test results through accessing said on-line application within said to enter the test subject's identifying information, including written information and photographic information of the test subject, the test subject's identification, the entirety of said test subject's oral collection immunoassay device indicating the test results through said visual readout, and the optional applied seal implement, wherein all of said written and photographic information is recorded and date- and time-stamped within said remote communication/photograph-taking device; and
   d) transferring said written documentation and said photograph information from said remote communication/photograph-taking device to said central depository, wherein said information is date- and time-stamped at said central depository upon receipt thereby;
   wherein said stored information is accessible for retrieval at a later date.

2. The system of claim 1 wherein said seal implement is present therein.

3. The system of claim 2 wherein said method includes the further steps of recording the unique identification of said seal implement and providing written documentation of said test subject onto said applied seal implement.

* * * * *